United States Patent [19]
Shields et al.

[11] Patent Number: 5,899,959
[45] Date of Patent: May 4, 1999

[54] MEASUREMENT OF VISUAL CHARACTERISTICS OF PAPER

[75] Inventors: William R. Shields, Newburgh, N.Y.; Kapil M. Singh, Erie, Pa.; James F. Suska, West Milford, N.J.; Ronald A. Stone, Warwick, N.Y.

[73] Assignee: International Paper Company, Purchase, N.Y.

[21] Appl. No.: 08/738,341

[22] Filed: Oct. 25, 1996

[51] Int. Cl.$^6$ .................................................. G01N 15/00
[52] U.S. Cl. ................................ 702/35; 356/237; 348/88
[58] Field of Search .............................. 364/525; 348/88, 348/92, 132; 382/112, 108, 110; 353/75; 432/1; 250/458.1; 702/35

[56] References Cited

U.S. PATENT DOCUMENTS

| | | | |
|---|---|---|---|
| 3,744,893 | 7/1973 | Chandler | 353/75 |
| 4,223,346 | 11/1980 | Neiheisel et al. | 358/106 |
| 4,415,926 | 11/1983 | Henry | 358/107 |
| 4,487,575 | 12/1984 | Jager et al. | 432/1 |
| 4,857,747 | 8/1989 | Bolton | 250/559 |
| 4,918,522 | 4/1990 | Pajunen | 358/101 |
| 4,922,337 | 5/1990 | Hunt et al. | 358/101 |
| 4,931,657 | 6/1990 | Houston et al. | 250/559 |
| 5,047,652 | 9/1991 | Lisnyansky et al. | 250/571 |
| 5,053,626 | 10/1991 | Tillotson | 250/458.1 |
| 5,068,799 | 11/1991 | Jarrett, Jr. | 364/507 |
| 5,305,392 | 4/1994 | Longest, Jr. et al. | 382/8 |
| 5,309,496 | 5/1994 | Winsor | 378/98.2 |
| 5,563,809 | 10/1996 | Williams et al. | 364/560 |
| 5,594,770 | 1/1997 | Bowles et al. | 378/58 |
| 5,661,817 | 8/1997 | Hatlestad et al. | 382/110 |

FOREIGN PATENT DOCUMENTS

| | | |
|---|---|---|
| 572336A1 | 5/1993 | United Kingdom . |
| 579461A1 | 7/1993 | United Kingdom . |

OTHER PUBLICATIONS

Shead, R. P., "Formation Measurement: How It Relates to the Process and Final Quality", Proceedings of the european Pulp and Paper Week 4th Internattional conference, New Available Technol9ogy Current Trends (Bologna), vol. 2, Paper Control, pp. 436–443, May 1992.

Muller, R., "controlling Quality at the Wet End—Formation Tester", Paper Technology Industry, vol. 30, No. 8, pp. 30–32, 34, Aug. 1989.

Shapiro, S.I., "On–Line Formaiton Sensors: Survey of Current Use", TAPPI Papermakers Conference (Washington, D.C.) Proceedings, pp. 149–152, Apr. 1989.

Kajaani Electronics, "Users Manual—Kajaani Formation Analyzer".

Trepanier, R. J., "formation Measurement with the Paprican Micro–Scanner", ObTest Equipment Inc., Third Printing, Hawkesbury, ON, Canada, Mar. 1993.

(List continued on next page.)

*Primary Examiner*—James P. Trammell
*Assistant Examiner*—Matthew Smithers
*Attorney, Agent, or Firm*—Luedeka, Neely & Graham, P.C.

[57] ABSTRACT

A paper web formation measurement system provides on-line measurement and control of visual properties of a moving web of paper. The measurement system includes an image acquisition system for capturing images of the moving web, and an image analysis system for analyzing captured images. The image acquisition system includes a strobe lighting system for backlighting the moving web and a charge injection device (CID) camera for capturing light transmitted through the web to form an image of the web in non-standard (non-RS-170), full frame format. Captured images are digitized by the image analysis system to 256 graylevel and analyzed to produce a mathematical formation index representing visual properties of the web. The mathematical formation index, which is derived from a graylevel distribution histogram, is presented to paper production personnel to enable on-line adjustment of process variables to maximize paper quality. The image analysis system is also configured to ascertain the distribution of flocs and voids within the image. The mathematical formation index may be adjusted to reflect the distribution of flocs and voids within the web.

17 Claims, 5 Drawing Sheets

OTHER PUBLICATIONS

Cresson, T., and Luner, P., "The Characterizaiton of Paper Formation. Part 2: The Texture Analysis of Paper Formation", Tappi Journal, vol. 73, No. 12, pp. 175–185, Dec. 1990.

Kajanto, I.M., Komppa, A., and Ritala, R.K., "How Formation Should be Measured and Characterized", Nordic Pulp and Paper Research Journal, vol. 4, No. 3, pp. 219–228, Oct. 1989.

Dufresne, L.L., "Update on a New On–Line Optical System for Formation Analysis", Canadian Pulp and Paper Association, Annual Meeting (Montreaul) Preprints 74A, pp. 257–260, Jan. 1988.

Kiviranta, A., Muinonen, K., Peltoniemi, J., Vahnala, H., and Karhumaa, J., "Measurement of Table Activity on a Fourdrinier Paper Machine: A New Photoclinometric Technique", Journal of Pulp and Paper Science, vol. 19, No. 6, pp. J226–J234, Nov. 1993.

Foyn, B., Papworth, S., "A Device for Measuring the Orientation of Paper Formation", Proceedings of European Pulp and Paper Week, 4th International Conference on New Availability Techniques and Trends, (Bologna, Italy), vol. 2 (Paper Control), pp. 425–435, May 19–22, 1992.

Saint Amand, F., J., Perrin, B. J., and Sabater, J. A., "Advanced Deinking Supervision Using a New Sensor for On–Line Speck Measurements", Quality Control, vol. 76, No. 5, Tappi Journal, pp. 139–146, May 1993.

Institute of Paper Science and Technology, The American Paper Institute Measurement Technology Program Report No. 73, Part II, Evaluation of On–Line formation Measuring Instruments, 1992.

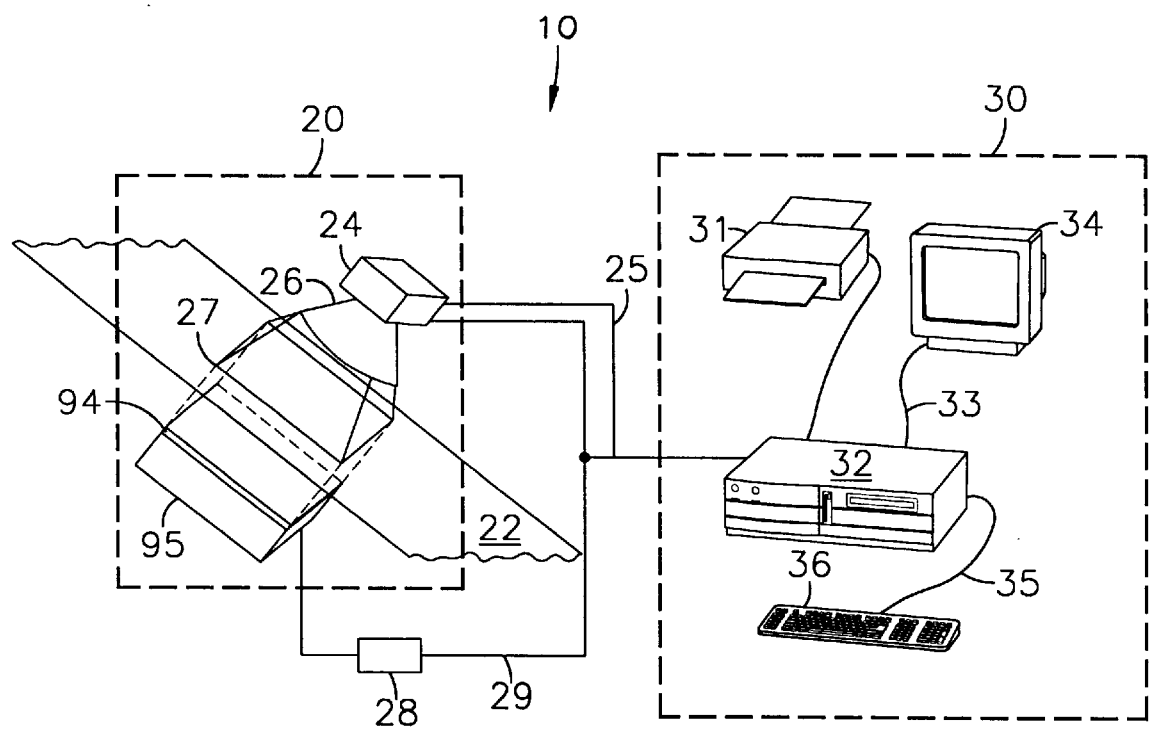
*Fig.* 1
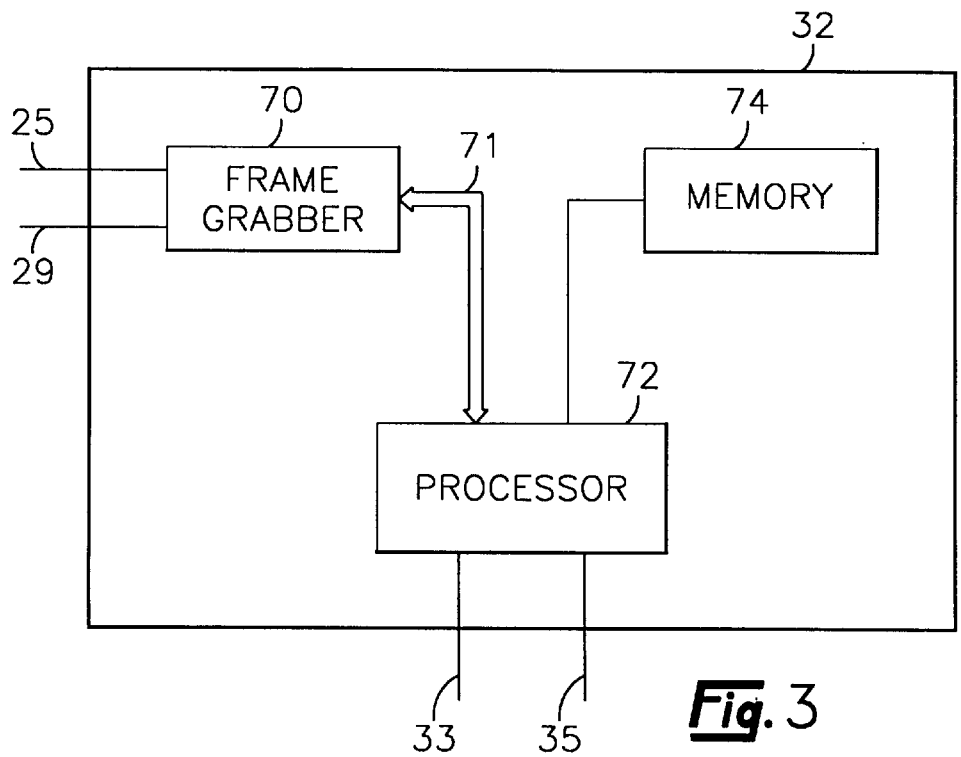
*Fig.* 3

MEASUREMENT OF VISUAL CHARACTERISTICS OF PAPER

TECHNICAL FIELD

The present invention relates to measurement of visual characteristics of paper, and particularly relates to measurement and control of paper formation, moisture streaks, wire marks, dirt, roughness, coating uniformity, gloss variation, and misregister in printing.

BACKGROUND

The production of paper involves many process variables which can affect paper quality and formation consistency. For example, the consistency of wood fibers and lignin content in the pulp can vary as wood from different types of trees is introduced into the stock. If, for example, lignin content increases or short fibers content decreases, machine settings must be commensurately adjusted and controlled to maintain consistency in the end product. Wood composition can vary even among trees of the same type growing in the same geographic location based on varying environmental factors such as soil composition, amount of sunlight, rain, etc.

As a further production variable, formation characteristics of paper are, to a large extent, unique to a particular papermaking machine. Papermaking machines are typically large with no two machines being built to the same specifications, dimensions, and operating speeds. Different machines are also operated and maintained differently. The result of these and other process variations in papermaking machines is that paper formation characteristics will vary in accordance with the particular machine used during paper production.

The many process variables involved in the manufacture of paper must be adequately and consistently controlled to avoid undesirable paper formation properties. Visual characteristics of the paper (including formation, moisture streaks, wire marks, dirt, roughness, coating uniformity, gloss variation, and misregister in printing) can provide much needed feedback for machine operators to adjust process variables in order to achieve a consistently high quality paper product. Unfortunately, current techniques fail to adequately monitor these visual characteristics in a manner that would enable machine operators to make needed production adjustments in an effective and efficient manner.

Control of process variables during production is also important because many processes today utilize recycled pulp, which varies significantly in the quantity of undesirables and in the consistency of fiber characteristics. Recycled pulp contains varying amounts of undesirables such as printing ink, polymers from coatings, dirt, and other contaminants. Also, fiber and lignin content vary significantly because recycled pulp is typically made from a variety of paper products that were also produced by different processes with different machines and from different wood sources. Therefore, production control can become even more critical to formation consistency when using recycled pulp.

A principle factor that has frustrated the evolution of a new generation of pulp control systems is the inability to accurately, reliably, and consistently observe visual characteristics of the paper product as it is formed. A common production control technique is to utilize human observation of the paper's visual characteristics. By holding a sample paper web up to a light source, one is able to observe, in general measure, formation consistency and other visual characteristics within the paper web. This type of direct human observation of the paper's visual characteristics provides a good general assessment of formation, but it is inconsistent and inefficient. Human observation is largely subjective and prior attempts to provide a system for valuating human observed characteristics are ineffective. Human assessment is ineffective because the human eye is unable to observe the paper web on-line as it speeds along the production machines. Instead, direct human observation must be performed on the end product, resulting in a production control solution that is slow, inefficient, and simply unable to respond to constantly changing process variables in a timely manner. What is needed is an automated on-line system for measuring, analyzing, and valuating visual characteristics of paper in a manner that closely approximates and complements human assessments. The system should be able to provide a single and consistent valuation, or index of the visual properties of the web.

Attempts have been made to provide an on-line system for measuring formation and other visual characteristics of paper. Formation is most commonly measured on-line with single point light or laser transmission. However, this technique does not allow proper correlation with human visual assessment or with off-line formation measurement testers, which extract formation measurements from two-dimensional images. Also, the results of the off-line testers are only available after the paper has been made and sampled from reels, and, therefore come too late for any kind of on-machine control of paper formation.

Other attempts in the art have involved the use of backlighting the paper web as it speeds along the machine. In a paper entitled "A Device for Measuring the Orientation of Paper Formation", Foyn et al. discuss analyzing the orientation of formation across a paper web at web speeds up to about 4900 feet per minute. The paper discusses use of a stroboscope to illuminate the web while a CCD (Charge Coupled Device) camera with a $1/10,000$ sec. shutter speed obtains data from the illuminated web. Data analysis is frequency-based and one-dimensional, and therefore lacks the ability to emulate human visual observation. Such systems suffer from various other drawbacks which limit their usefulness, particularly in high speed applications including, but not limited to, focus and motion jitter problems.

U.S. Pat. No. 5,068,799 to Jarrett, Jr. describes a method for detecting flaws in a continuous moving web of cloth material moving at speeds of up to 600 feet per minute by using a high intensity light to backlight the material. Data obtained with a video camera is then compared against stored templates of known flaws. However, the system is not useful in high speed on-line applications for providing real time control capability.

It is therefore an object of the present invention to provide a method and apparatus for measuring visual characteristics of a moving web of paper, including a web forming on a paper machine wire, and analyzing the resulting data on-line and during production to enable machine operators to make necessary control adjustments in a consistent and efficient manner.

Another object of the present invention is to provide a method and apparatus for on-line measurement of visual characteristics of a moving web of paper, including a forming web on a paper machine wire, and on-line analysis of the resulting data in a manner that closely approximates human assessment of the web's visual characteristics.

Another object of the present invention is to provide a method and apparatus capable of measuring visual characteristics of a paper web and producing an objective and consistent valuation, or index, of the web's visual characteristics.

Another object of the present invention is to provide a method and apparatus for measuring visual characteristics of a paper web on-line while the web is moving at speeds up to 5,000 feet per second.

Another object of the present invention is to provide a method and apparatus for measuring, analyzing, and displaying visual characteristics of a high speed web of paper with a video camera that does not induce motion jitter in the captured image.

Another object of the present invention is to provide a method and apparatus for measuring visual characteristics of a high speed web of paper with a video camera, and keeping the web in focus with the camera even as the web flutters.

Another object of the present invention is to provide a method and apparatus for on-line determination of a mathematical formation index corresponding to formation consistency in a moving web of paper.

Finally, it is an object of the present invention is to provide a method and apparatus for on-line determination of the areal composition of flocs and voids within a web of paper moving at a high speed on a papermaking machine.

SUMMARY

With regard to the foregoing and other objects, the present invention provides in one aspect an apparatus for determining visual characteristics of a paper web having opposed first and second surfaces. The apparatus includes an image acquisition system for acquiring images of the paper web and a computer analysis system for analyzing the acquired images. The image acquisition system includes a strobe for producing flashes comprised of light. The strobe is positioned to illuminate a section of the first surface of the paper web during each flash. At least a portion of the light from each flash is transmitted through the web to the second surface, illuminating a section of the second surface with the transmitted light. An array camera is positioned adjacent the second surface to receive the transmitted light and produce video signals corresponding to a full frame, two-dimensional image of the illuminated second surface.

The computer analysis system includes a framegrabber circuit for initiating the image acquisition system, receiving the video signals from the array camera, digitizing the video signals, and holding the digital video signals for display and analysis. A digital data processor controls the framegrabber circuit to cause the circuit to initiate the image acquisition system and to output the digital video signals for display and analysis. The data processor includes means for analyzing the digital video signals to produce an optical distribution of the transmitted light.

A number of analysis features may be added to the basic apparatus described above. For example, the data processor may further include means for producing a mathematical formation index of the measured web based on the optical distribution of transmitted light. As another example, the means for analyzing may include means for determining the size distribution of flocs and voids in the web.

To limit the adverse effects of ambient light impinging on the camera, a shield may be positioned around the camera. The shield includes an opening between the camera and second surface of the web to allow the camera to image the web. The shield further serves to protect the camera from contaminants that are typically expelled from the paper web as the web moves at high speeds.

According to another aspect, the invention provides a method of measuring visual properties of a moving web having oppositely oriented first and second surfaces. The method includes the steps of illuminating a two-dimensional section of a first surface of the web with light. Some of the light will be transmitted through the web and distributed across a two-dimensional section of the web where the distribution of transmitted light will correspond to a range of graylevel values having a minimum graylevel value and a maximum graylevel value. Analog video signals, corresponding to a full frame video image of the two-dimensional web section and representing the intensity of the transmitted light, are produced from the transmitted light. The analog video signals are then digitized and analyzed to produce an optical distribution of the transmitted light throughout the two-dimensional web section. From this optical distribution, a mathematical formation index corresponding to human visual ranking of the two-dimensional section of the web is produced.

For on-line applications, the method also includes the step of adjusting paper production process variables to maximize the formation index.

An historical record of web measurements may be obtained by storing a time series of mathematical formation indices. Graphical representations of the stored formation indices can be produced and displayed. In on-line applications, production personnel utilize the graphical representation to adjust production variables in order to obtain desired pulp and paper properties.

Analysis of the digital video signals preferably includes generating a histogram representing the distribution of graylevel values within the image. The histogram is generated by partitioning the range of graylevel values into a plurality of graylevel bins where each bin contains two or more consecutive graylevels. Each of the digital video signals are then allocated to a corresponding bin to produce the optical distribution of transmitted light.

After each of the video signals has been assigned to a bin, the mathematical formation index is produced by identifying a mean graylevel bin within the histogram. The total number of video signals allocated to the mean bin are summed to produce a first number. The number of bins that contain more than a predetermined number of digital video signals are summed to produce a second number. The first number is then divided by the second number to produce the mathematical formation index.

The method may further include steps to adjust the mathematical formation index so that it reflects the size distribution of flocs and voids within the web. To account for floc size distribution, a second histogram is generated that represents the size distribution of flocs within the image. A floc threshold value is determined and compared to each of the digital video signals. All video signals having a graylevel value greater than the floc threshold are eliminated, leaving only video signals that represent likely flocs. Contiguous floc video signals are grouped together and each group is considered to be a floc. A floc size threshold is determined. A floc surface area for each floc is also determined. The floc size threshold is then compared to the surface area of each floc and flocs having surface areas smaller than the threshold are eliminated. The range of surface areas are partitioned to produce a plurality of floc size bins where each bin contains a subrange within the range of floc sizes. Each of the remaining flocs are allocated to a corresponding floc size bin to produce the second histogram.

The distribution of floc sizes within the second histogram is then used to adjust the mathematical formation index. The formation index is normalized by multiplying by a first value corresponding to an acceptable floc distribution of the web. The number of floc size bins between the lowest floc size bin that contains flocs and the highest floc size bin containing flocs are summed to produce a second value. The normalized mathematical index is then divided by the second value to produce a mathematical formation index representative of the distribution of flocs within the image. If the web contains a normal distribution of floc sizes, the mathematical formation index will not change. If the web contains a good or favorable distribution of floc sizes, the mathematical formation index will increase to reflect the favorable floc size distribution.

BRIEF DESCRIPTION OF PREFERRED EMBODIMENTS

Preferred embodiments of the invention will now be described in further detail with reference to the drawings wherein like reference characters designate like or similar elements throughout the several drawings as follows:

FIG. 1 is a diagrammatic illustration of a paper formation measurement system, including an image acquisition system and an image analysis system;

FIG. 3 is a functional block diagram of the image analysis system computer;

DETAILED DESCRIPTION OF PREFERRED EMBODIMENTS

Figure 2:
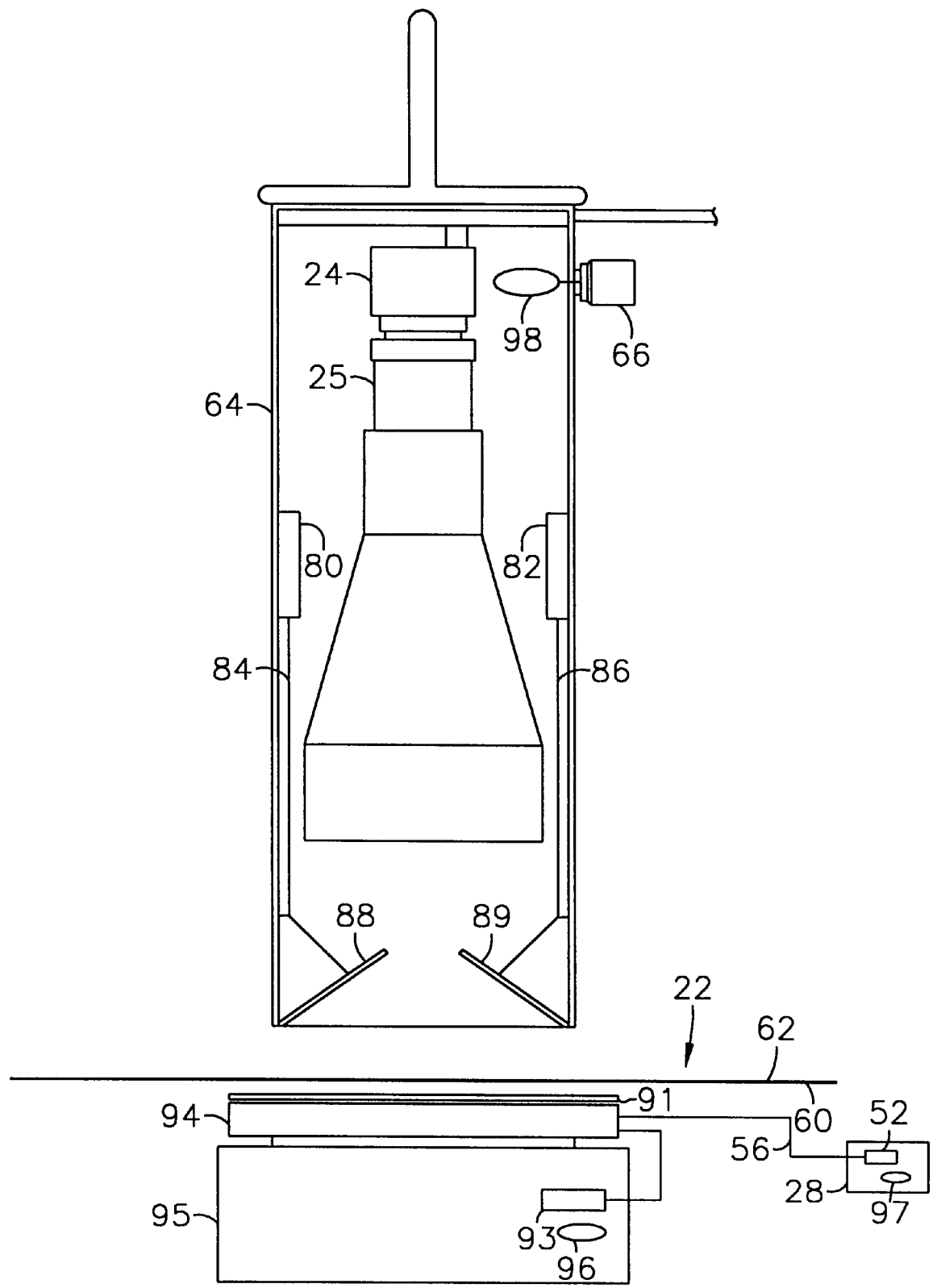
FIG. 2 is a side view of the image acquisition system of FIG. 1.

A preferred embodiment of a paper web formation measurement system 10 is illustrated in FIG. 1. The embodiment of FIG. 1 illustrates an on-line application of the invention for measuring and controlling visual properties of a moving web of paper 22 during production including formation, moisture streaks, wire marks, dirt, roughness, coating uniformity, gloss variation, and misregister in printing. The system 10 is capable of measuring these visual web properties at web speeds of up to 5,000 feet per minute. It will be understood, however, that the system 10 may also be employed in off-line applications to measure the visual formation properties of a stationary paper web.

As FIG. 1 illustrates, the apparatus of the invention consists of two main parts: (1) an image acquisition system 20, and (2) an image analysis system 30. The image acquisition system 20 includes a camera 24 for capturing images, or frames of the web 22. Preferably, the camera 24 is a ⅔ inch charge injection device (CID) video camera that generates a non-standard (i.e., non RS-170), 30 Hz, sequential scan, full frame video output with a 512×512 pixel array. The use of full frame video eliminates motion jitter induced by standard video cameras that display images in an odd and even raster pattern. In standard RS-170 video cameras, motion jitter results from the time delay between generation of the odd scan and the even scan on the video display. Even high speed framegrabbers exhibit this problem since they can capture the frame in real time but still must display it with RS-170 limitations. The typical solution to eliminating motion blur is to utilize what is commonly referred to as a motion blur filter, which essentially extrapolates the image between odd and even scans. The CID camera 24 of the present invention eliminates the need for a motion blur filter.

The camera 24 is timed to a strobe flash unit 28 that produces and conducts light to a light distribution plate 94 to provide high intensity illumination of a two-dimensional section 27 of the web 22. As illustrated in the more detailed drawing of FIG. 2, light plate 94 is supported by a support stand 95 and is fitted with an air-activated, computer controlled protective door 91 that opens and closes in response to the presence/absence of paper 22. A paper sensor 93 is employed so that the system will know when the paper 22 is present and when it is absent. A paper out condition places the system in idle. The light plate door 91, as well as doors 88 and 89, close to protect the light plate 94 and camera 24 and no measurements are taken until paper 22 is present again. The paper sensor 93, strobe flash unit 28, and camera 24 are cooled by air supplied vortex coolers, shown generally at 96, 97, and 98.

The strobe flash unit 28, which is preferably remote to the light plate 94, includes a strobe flash 52 for producing short duration (preferably 8 microsecond) light pulses which are transmitted to the light distribution plate 94 via a fiber optic cable 56. The strobe flash unit 28 provides a light output pulse of 8 microsecond duration at all energy settings. Flash repetition rate is variable to 200 flashes per second with a broadband light output of 20 millijoules per flash. Each flash is initiated by a TTL or differential voltage pulse that is received from camera 24 on line 29.

With continued reference to FIGS. 1 and 2, light pulses output by the strobe flash unit 28 illuminate the surface 60 of the web that is adjacent to the flash unit 28. The paper web 22, being translucent, transmits some of the light through the web 22 with the transmitted light exiting the web surface 62 that is oppositely oriented to surface 60 and adjacent the camera 24. Thus, each flash produces an illuminated section 27 of the web 22 for imaging by the camera 24.

The amount of light actually transmitted through the web 22 at any point is a direct function of the formation properties of the web 22. For example, the amount and intensity of light transmitted through a floc (heavier than critical basis weight) will be less than the amount and intensity of light transmitted through a void (lighter than critical basis weight). Similarly, if dirt is present in the web 22 it will tend to block the transmission of light through the web 22. By imaging the distribution of transmitted light at the illuminated section 27 of the web 22, the system 10 measures the visual formation properties of the web 22 in much the same way as when a paper web is held up to a light source and observed by a human eye.

As illustrated in FIG. 2, the camera 24 is positioned within a cover box 64 that provides several functions. A newly formed or coated paper web will typically propel various particulates as the web speeds along the machinery. The cover box 64 protects the camera 24 and its attached optics from contamination by these particulates. Particulates are also prevented from reaching the camera 24 and its optics by maintaining positive atmospheric pressure, relative to ambient, within the cover box 64 and by employing air activated, computer controlled doors 88 and 89, which open and close by actuators 80, 82 and associated linkages 84, 86 in response to the presence/absence of paper 22.

Pressurizing air is provided at inlet 66. Air provided to the cover box 64 serves to cool the camera 24 as well. The cover box 64 also functions as a dead light space for the camera 24 by blocking out ambient light that would otherwise interfere with the camera's ability to capture only light that is transmitted through the illuminated section 27 of the web 22. The inside portion of the cover box 64 is painted black to further reduce the effects of ambient light.

In a preferred embodiment, the attached optics include a base lens 25 and a custom, optical comparator, telecentric, gauging lens 26. An Invitar™ telecentric gauging lens manufactured by Melles Griot has been found to be particularly suitable. This combination of optics provides a 4 inch by 4 inch field of view of the illuminated web section 27 at a working distance of 8 inches.

During production, paper webs moving at high speeds through the production machinery tend to flutter up and down. The camera's depth of field should therefore be large enough to ensure that the web 22 will remain in focus in the event the web 22 flutters. The telecentric lens 26 provides less than 2% maximum distortion at the camera's array with a depth of field of about 0.50 inches. This depth of field and maximum distortion level allows the image to remain in focus even if the paper web flutters up or down as much as 0.25 inches from its usual position.

To capture an image, or frame of the illuminated section 27, light transmitted through the illuminated section 27 is focused by the camera's lenses 25, 26 onto an array of light sensitive elements, or pixels within the camera 24. In a preferred embodiment, the camera includes an array of 512×512 pixels for a total count of 262,144 pixels per frame. Each pixel receives light transmitted through the illuminated section 27 and outputs an analog voltage proportional to the average amount of light striking the pixel. The pixel voltages are output by the camera 24 on lines 25 to the image analysis system 30 for processing and analysis, as will be further described herein.

With continued reference to FIG. 1, the image analysis system 30 consists of a computer 32, a CRT display 34, and a keyboard 36 or comparable user input means. FIG. 3 provides a block diagram illustration of the computer 32, which includes a digital processor 72, a framegrabber circuit 70, a PCI bus 71, and electronic memory 74 such as a hard drive for storage of image data. Preferably, the framegrabber 70, processor 72, and bus 71 are high speed devices to enable frames to be grabbed at high web speeds. In a preferred embodiment, the processor 72 is a 100 MHz Pentium processor with PCI bus interface capability, and the framegrabber 70 is a 32-bit, PCI BitFlow Raptor framegrabber. Bus 71 is a PCI bus, enabling high speed image transfer. The hardware of this preferred embodiment enables full frame video images to be captured at web speeds of up to 5,000 feet per minute. Of course, advances in digital processor and framegrabber technology will enable the system 10 of the present invention to capture images at even higher web speeds.

To capture an image, the framegrabber 70 initiates the image acquisition system 20 by transmitting a TTL or differential voltage pulse to camera 24. In response, the camera 24 blanks all pixel registers (resets to zero) and commands the strobe flash unit 28 to output an 8 microsecond pulse of light. The camera's array of pixels receives light transmitted through the illuminated section 27 of the web 22 as previously discussed and registers an analog voltage for each pixel corresponding to the average amount of light received by the pixel.

The camera 24 outputs the analog pixel voltages to the framegrabber 70 where an analog-to-digital converter converts the voltages to a digital gray level value corresponding to the average amount of transmitted light received by the pixel. Preferably, an 8-bit analog-to-digital converter is utilized, resulting in a range of $2^8$, or 256 (0 to 255) possible gray level values ranging from black (no light transmitted to the pixel) to white (pixel saturated with light). In a preferred embodiment, black is assigned a graylevel value of zero and white is assigned the highest graylevel value of 255 so that the more light that is received by a pixel, the higher will be the resulting graylevel value for that pixel.

In high ambient light environments, the camera's pixel registers will begin to register ambient background light between blanking and strobe initiation. To eliminate this possible source of error, the background light is measured, stored, and then subtracted from the graylevel value for each pixel.

A formation index representing the visual properties of the imaged web section 27 is calculated from the distribution of graylevels throughout the captured frame. The formation index is calculated from a histogram derived from the graylevel value distribution. The histogram is derived by creating a plurality of bins with each bin representing a range of graylevel values and then assigning each of the graylevels within the frame to its corresponding bin. After the binning of graylevel values is complete, each bin within the histogram will contain a count of the total number of pixels within the frame having graylevel values corresponding to that bin range. For example, a preferred embodiment utilizes 128 bins with each bin having a range of two graylevel values assigned to it so that bin 1 contains a count of all pixels within the frame having graylevel values of either 0 or 1, bin 2 contains a count of graylevel values of 2 and 3, and continuing in like manner up to bin 128 which contains a count of the graylevel values of 254 and 255. Alternatively, the range of each bin could be greater or less than two graylevels, depending on the sensitivity desired. For example, a bin range of 4 graylevels per bin would result in a total of 64 bins.

Figure 4:
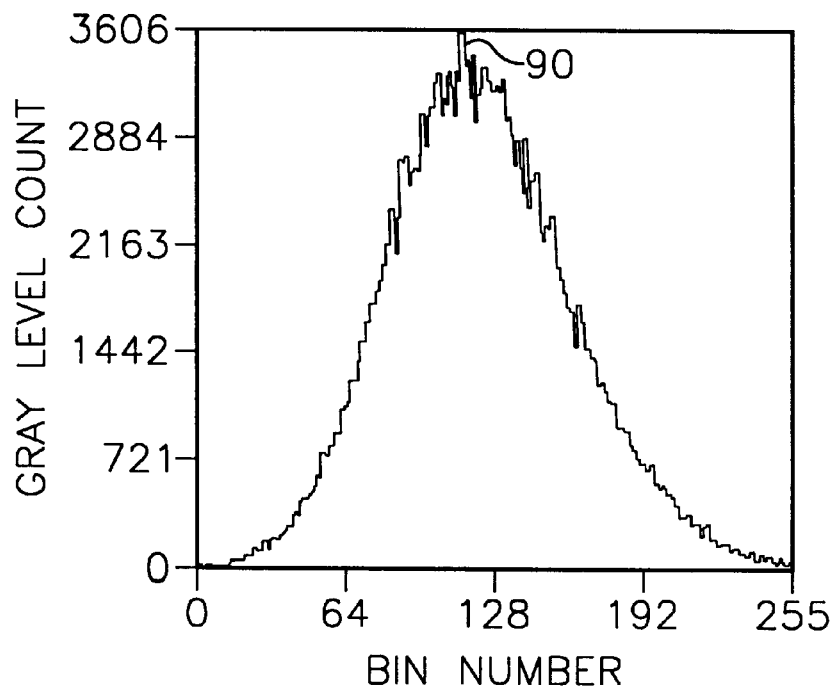
FIG. 4 is a histogram illustrating the distribution of graylevel values within an image of a paper web having typical formation properties.
Figure 5:
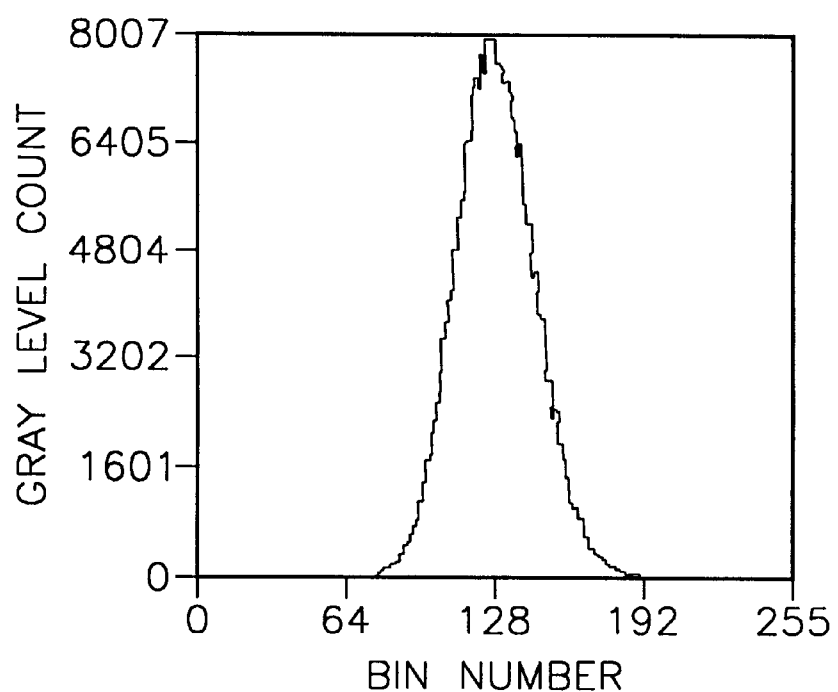
FIG. 5 is a histogram illustrating the distribution of graylevel values within an image of a paper web having more favorable formation properties than the paper web of FIG. 4.

FIG. 4 illustrates a typical 128 bin histogram showing the distribution of light within the frame. Generally, poor web formation characteristics will result in widely varying graylevel distributions, while good formation characteristics will result in a more even transmission of light through the illuminated section 27 of the web 22 resulting in a high concentration of graylevel counts near the center bin, indicated generally at 90. Typically, it is desirable to force the center of graylevel distribution toward the graylevel mean so that a Gaussian distribution of graylevels results. With a Gaussian distribution of graylevels within the histogram, the better the formation characteristics of the paper web 22, the greater will be the frequency of graylevels at the distribution mean. In other words, to maximize paper formation characteristics one would want to adjust process variables to force the distribution of graylevel values within the histogram toward the distribution mean 90 so that the distribution height at the mean 90 is much greater than the width of distribution from the mean 90. For purposes of relative comparison, the histogram of FIG. 5 exhibits a more favorable distribution of graylevels than the histogram of FIG. 4.

The formation index (FI) is calculated from the histogram by totaling the three bins containing the greatest number of counts and then dividing that total by the number of bins that contain more than a predetermined number of counts (X), as given by the following equation:

$$FI = \text{no. of pixels for 3 largest bins/no. of bins with more than } X \text{ pixels} \quad (1)$$

The variable X in Equation 1 above is 250 in a preferred embodiment. However, the actual value selected will depend on the sensitivity desired as well as the total number of pixels in the frame.

The measured formation index is provided to machine operators every minute, for example, to enable the operators to take necessary steps to optimize the paper making process. A web 22 that exhibits good formation characteristics will produce a high formation index, while a poorly formed web 22 will result in a lower formation index. Therefore, the index provides a single, objective valuation of the formation characteristics of the paper web 22 that closely approximates human visual ranking of paper. A significant improvement over human visual ranking is achieved, however, since the formation index provided by the present invention can be derived on-line at web speeds up to 5,000 feet per minute. Since the index is derived from on-line measurement of a moving web 22, it can be used by machine operators in a timely manner to adjust process variables as necessary to achieve the highest paper formation quality possible. The index is objective and consistent, which enables machine operators to make process adjustments efficiently and reliably.

The formation index may be provided to machine operators in a variety of formats. In one format, computer 32 is programmed to store formation indices derived from web images over a time period of paper production, and to plot the measured indices in a graphical format that is displayed on monitor 34 so that machine operators are provided with a recent history of paper quality as represented by the formation indices. A hardcopy of the formation index graph may be printed on printer 31.

Figure 6:
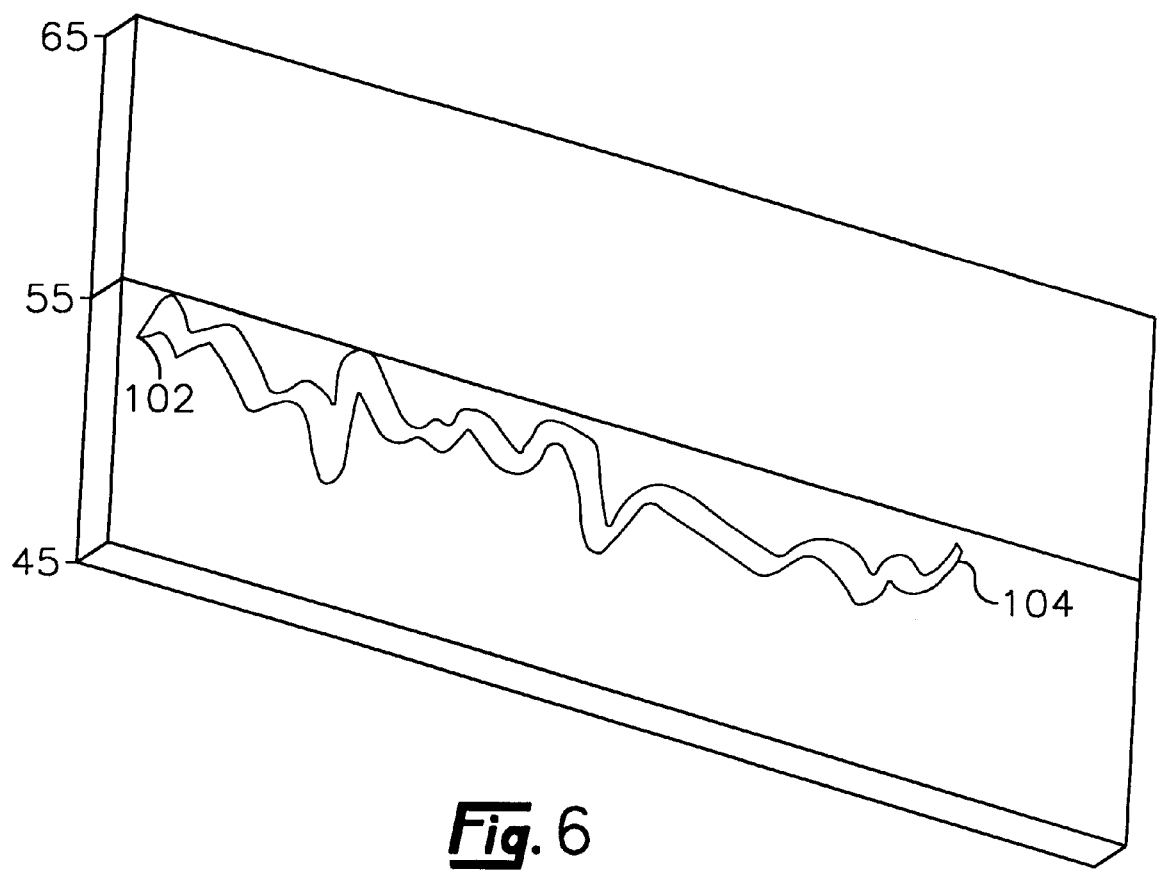
FIG. 6 is a perspective view of a graph showing the thirty most recently measured formation indices.

FIG. 6 illustrates a typical graph of measured formation indices. The graph of FIG. 6 represents a plot of the thirty most recent formation index measurements, or data points 102, 104, where data point 102 is the most recent data point and data point 104 is the oldest of the thirty data points. As new data points are added to the graph, the oldest data points are eliminated. Preferably, each of the thirty data points represents an average of two or more measurements so that the graph presents operators with an average valuation of the formation properties of the web. For the graph of FIG. 6, each data point was determined by averaging thirty consecutive index measurements. The graph also provides operators with an average of the thirty data points presented in the graph, approximately one hour runtime and a long term (24 hour) history graph.

Referring again to FIG. 4, the histogram provides little insight into the distribution of flocs and voids with the web 22. A web 22 that exhibits a favorable formation index in accordance with the histogram of FIG. 5 could be replete with flocs and voids. Thus, computer 32 is programmed to determine the distribution of flocs and voids within the illuminated section 27 of the web 22 from the distribution of graylevels within the image. A floc is generally characterized as an area of the web 22 where a relatively higher density of fibers (greater than critical basis weight) have formed, thus creating an area of the web 22 that is more opaque, or darker than other areas. A void is generally characterized as an area of low fiber density (lighter than critical basis weight), creating an area of low opacity. From the histogram of FIG. 4, critical basis weight may be determined by averaging the three bins nearest the distribution mean 90.

Flocs are identified by determining a threshold graylevel value (floc threshold) and comparing each graylevel value of the image to the floc threshold. The floc threshold may vary, depending on the darkness or lightness of flocs that are being searched. Generally, when searching for dark flocs, a lower floc threshold is selected than when searching for light flocs.

Each graylevel value of the image is compared to the floc threshold, and all graylevels that are greater than the floc threshold are eliminated from further consideration of floc distribution. For example, for a floc threshold of 175, every graylevel greater than 175 is assumed to not be representative of a floc and eliminated from the image. All contiguous pixels meeting the floc threshold are assumed to be representative of a floc. Contiguous pixels forming flocs are traced at their perimeters and analyzed to determine the surface area of each floc. Flocs that measure below a threshold size are considered too small for concern and eliminated from further consideration. The remaining pixels provide a representation of the distribution of flocs within the imaged section 27 of the web 22 and can be provided to machine operators by display on monitor 34 or printed in hardcopy on printer 31.

The floc size threshold will vary, depending on the type of paper that is being analyzed. For many types of paper, a size threshold of 0.5 mm$^2$ is preferred. However, when analyzing fine paper a smaller threshold should be used.

To determine the distribution of voids (lighter than critical basis weight) within the illuminated section 27 of the web 22, a process similar to that just described for floc distribution is used, except a different graylevel threshold (void threshold) representing a lighter area of the web 22 is used for graylevel comparison. For example, a void threshold of 185 could be compared to each graylevel of the image. All pixels having a graylevel value less than 185 would be considered representative of a non-void area and eliminated from further consideration of void distribution. Contiguous pixels having a combined surface area of, for example, 0.5 mm$^2$ or greater would be retained as representative of voids. The resulting void distribution could be displayed on monitor 34 or printed on printer 31.

Figure 7:
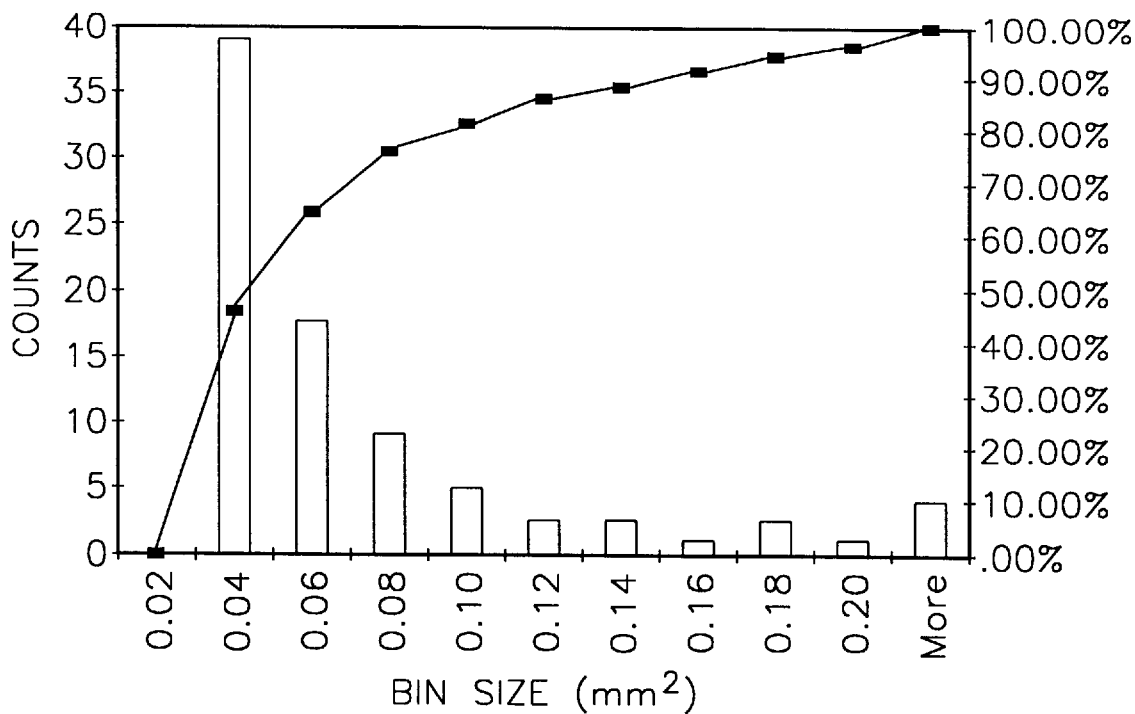
FIG. 7 is a histogram illustrating the distribution of floc sizes within an image of a paper web.

When floc and void distribution is a relevant consideration of paper quality, the formation index (FI) may be adjusted to reflect the distribution of flocs and/or voids within the web 22. This is accomplished by generating a second histogram based only on the size of flocs or voids. For example, to adjust the FI to reflect floc distribution, a floc size distribution histogram like the one illustrated in FIG. 7 is generated where each bin is incremented in 0.02 mm$^2$ steps so that bin 1 contains a count of flocs having a total surface area of less than 0.02 mm$^2$, bin 2 contains a count of flocs having a total surface area of 0.02 to 0.04 mm$^2$, and continuing in like manner up to the tenth bin 110 which contains a count of flocs having a total surface area of 0.18 to 0.2 mm$^2$. Similarly, a void size distribution histogram like the one illustrated in FIG. 8 is generated to adjust the FI to reflect void distribution.

Generally, a web 22 exhibiting a favorable floc or void distribution will produce a floc/void size distribution histogram having a distribution width of ten or less bins, where the distribution width is equal to the total number of bins between the low size bin (contains one or more flocs/voids representing the smallest flocs/voids within the image) and the high size bin (contains one or more flocs/voids representing the largest flocs/voids within the image) inclusive.

Figure 8:
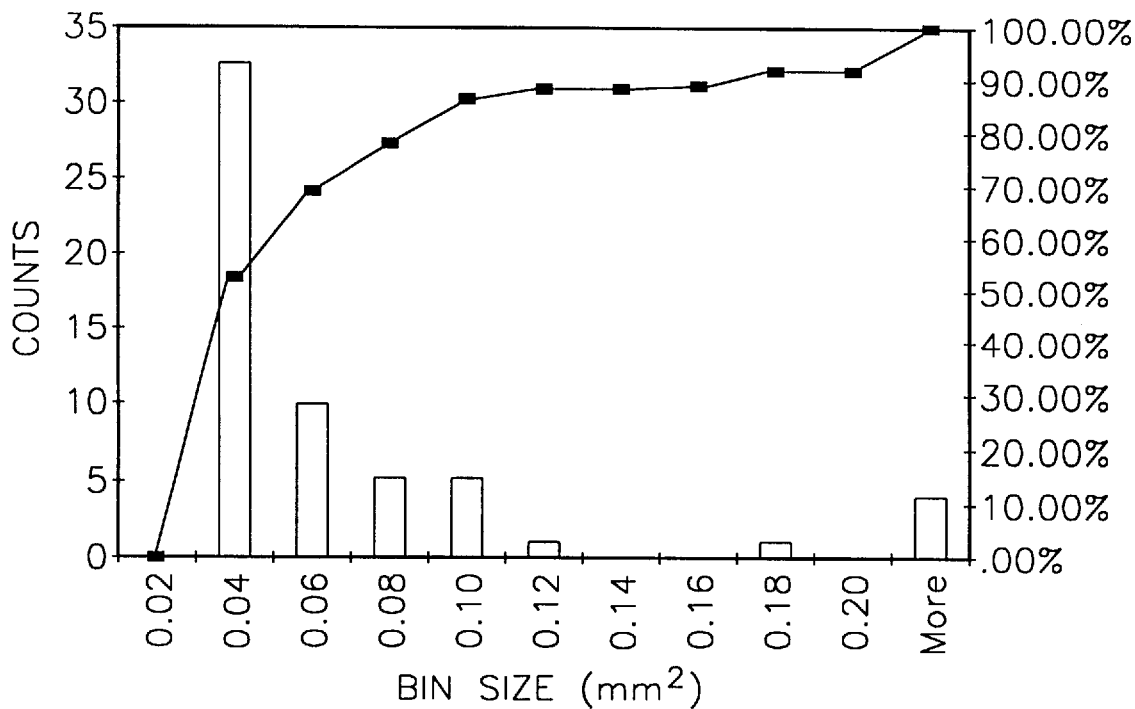
FIG. 8 is a histogram illustrating the distribution of void sizes within an image of a paper web.

Therefore, for the histograms of FIGS. 7 and 8, the interest is primarily in the width of floc/void distribution rather than how many flocs are in a given bin. The FI can be adjusted to reflect floc and/or void distribution by normalizing the FI (preferably, multiply by 10) and dividing the normalized FI by the floc/void distribution width.

For example, to adjust the FI to reflect the distribution of flocs as reflected in the histogram of FIG. 7, the FI is multiplied by the factor "10" and the result is divided by the number of bins in the histogram that contain one or more flocs. A web 22 exhibiting favorable floc distribution will normally have 10 or less bins that contain flocs. Therefore, if 10 bins contain flocs, the FI will be divided by "10" and there will be no change to the FI. If only 8 bins contain flocs (more favorable floc distribution than 10 bins), the FI will increase to reflect the more favorable floc distribution. If 13 bins contain flocs (less favorable floc distribution than 10 bins), the FI will decrease to reflect the less favorable floc distribution. In like manner, the FI may be adjusted to reflect the distribution of voids (FIG. 8) within the web 22. Of course, the FI may also be adjusted by this procedure to reflect both floc and void distribution.

It is contemplated, and will be apparent to those skilled in the art from the foregoing specification, drawings, and examples that modifications and/or changes may be made in the embodiments of the invention. Accordingly, it is expressly intended that the foregoing are illustrative of preferred embodiments only, not limiting thereto, and that the true spirit and scope of the present invention be determined by reference to the appended claims.

What is claimed is:

1. An apparatus for determining visual characteristics of an uncoated paper web having opposed first and second surfaces, the apparatus comprising:
    an image acquisition system having:
        a strobe for producing flashes comprised of light, said strobe positioned to illuminate a section of the first surface of the paper web during each flash, wherein at least a portion of the light comprising each flash is transmitted through the web to the second surface to illuminate, with the transmitted light, a section of the second surface adjacent to the illuminated section of the first surface; and
        a charge injection device camera positioned adjacent the second surface to receive the transmitted light and produce video signals corresponding to a full frame, two-dimensional image of at least a portion of the illuminated second surface; and
    a computer analysis system having:
        a framegrabber circuit for initiating the image acquisition system, receiving said video signals, digitizing said video signals to produce digital video signals, and holding said digital video signals for display and analysis; and
        a digital data processor for controlling said framegrabber circuit to cause said circuit to initiate the image acquisition system and output the digital video signals for display and analysis, said data processor including means for analyzing said digital video signals to produce an optical distribution associated with the transmitted light illuminating the second surface.

2. The apparatus of claim 1, wherein said data processor further comprises means for producing a mathematical formation index corresponding to formation consistency in the web based on said optical distribution.

3. The apparatus of claim 1, further comprising a display for displaying at least said two-dimensional image.

4. The apparatus of claim 1, further comprising a printer for printing at least said two-dimensional image.

5. An apparatus for determining visual characteristics of a paper web having opposed first and second surfaces, the apparatus comprising:
    an image acquisition system having:
        a strobe for producing flashes comprised of light, said strobe positioned to illuminate a section of the first surface of the paper web during each flash, wherein at least a portion of the light comprising each flash is transmitted through the web to the second surface to illuminate, with the transmitted light, a section of the second surface adjacent to the illuminated section of the first surface; and
        an array camera positioned adjacent the second surface to receive the transmitted light and produce video signals corresponding to a full frame, two-dimensional image of at least a portion of the illuminated second surface; and
    a computer analysis system having:
        a framegrabber circuit for initiating the image acquisition system, receiving said video signals, digitizing said video signals to produce digital video signals, and holding said digital video signals for display and analysis; and
        a digital data processor for controlling said framegrabber circuit to cause said circuit to initiate the image acquisition system and output the digital video signals for display and analysis, said data processor including means for analyzing said digital video signals to produce an optical distribution associated with the transmitted light illuminating the second surface, said means for analyzing including means for determining the size distribution of flocs and voids in the web.

6. The apparatus of claim 5, wherein said data processor further comprises means for producing a mathematical formation index based on said optical distribution and said size distribution.

7. A method of measuring visual properties of a moving, uncoated web having oppositely oriented first and second surfaces, the method comprising the steps of:
    illuminating a two-dimensional section of a first surface of the web with light, at least a portion of said light penetrating said web and exiting the web at a two-dimensional section of a second surface of the web oppositely oriented to said first surface of the web, producing transmitted light distributed across the two-dimensional section, said distribution of transmitted light corresponding to a range of graylevel values having a minimum graylevel value and a maximum graylevel value;
    producing analog video signals from the transmitted light corresponding to a full frame video image of the two-dimensional section of the second surface, each of said analog video signals representing the intensity of transmitted light at a position of the two-dimensional section of the second surface;
    digitizing said analog video signals to produce digital video signals, each of said digital video signals representing a graylevel value corresponding to the intensity of the transmitted light;
    analyzing the digital video signals to produce an optical distribution of the transmitted light throughout the two-dimensional section of the second surface; and
    producing a mathematical formation index corresponding to formation consistency in the web from the optical distribution, said index corresponding to a human visual ranking of the two-dimensional section of the second surface of the web.

8. The method of claim 7, further comprising the steps of:
storing a time series of mathematical formation indices;
producing a graphical representation of said time series of mathematical formation indices; and
displaying said graphical representation.

9. The method of claim 8, further comprising the steps of:
averaging said time series of mathematical formation indices to produce an average index; and
displaying said average index.

10. The method of claim 7, wherein said analyzing step further comprises the step of generating a first histogram representing the distribution of graylevel values within the image by:
partitioning said range of graylevel values to produce a plurality of graylevel bins, each of said graylevel bins containing two or more consecutive graylevels; and
allocating each of said digital video signals to a bin corresponding to the graylevel value of the digital video signal, producing said optical distribution of the transmitted light.

11. The method of claim 10, wherein said producing step further comprises the steps of:
identifying a mean graylevel bin of the first histogram;
summing the number of digital video signals allocated to the mean graylevel bin, producing a first number;
summing the number of bins that contain more than a predetermined number of digital video signals, producing a second number; and
dividing the first number by the second number to produce said mathematical formation index.

12. The method of claim 7, further comprising the step of displaying at least said video image.

13. The method of claim 7, further comprising the step of printing at least said video image.

14. A method of measuring visual properties of a moving web having oppositely oriented first and second surfaces, the method comprising the steps of:
illuminating a two-dimensional section of a first surface of the web with light, at least a portion of said light penetrating said web and exiting the web at a two-dimensional section of a second surface of the web oppositely oriented to said first surface of the web, producing transmitted light distributed across the two-dimensional section, said distribution of transmitted light corresponding to a range of graylevel values having a minimum graylevel value and a maximum graylevel value;
producing analog video signals from the transmitted light corresponding to a full frame video image of the two-dimensional section of the second surface, each of said analog video signals representing the intensity of transmitted light at a position of the two-dimensional section of the second surface;
digitizing said analog video signals to produce digital video signals, each of said digital video signals representing a graylevel value corresponding to the intensity of the transmitted light;
analyzing the digital video signals to produce an optical distribution of the transmitted light throughout the two-dimensional section of the second surface and generating a first histogram representing the distribution of graylevel values within the image by:
partitioning said range of graylevel values to produce a plurality of graylevel bins, each of said graylevel bins containing two or more consecutive graylevels; and
allocating each of said digital video signals to a bin corresponding to the graylevel value of the digital video signal, producing said optical distribution of the transmitted light;
producing a mathematical formation index from the optical distribution, said index corresponding to a human visual ranking of the two-dimensional section of the second surface of the web, said mathematical formation index being produced by:
identifying a mean graylevel bin of the first histogram;
summing the number of digital video signals allocated to the mean graylevel bin, producing a first number;
summing the number of bins that contain more than a predetermined number of digital video signals, producing a second number; and
dividing the first number by the second number to produce said mathematical formation index;
generating a second histogram representing the size distribution of flocs within the image by:
determining a floc threshold value;
comparing the floc threshold value to each of said digital video signals;
eliminating all digital video signals having a graylevel value greater than the floc threshold so that only floc video signals remain;
designating groups of contiguous ones of the floc video signals as flocs;
determining a floc size threshold;
determining a floc surface area within a range of surface areas for each designated floc;
comparing the floc size threshold to the surface area of each floc;
eliminating all flocs having a surface area less than said size threshold;
partitioning said range of surface areas to produce a plurality of floc size bins, each of said floc size bins containing a subrange within the range of floc sizes; and
allocating each of said flocs to a floc size bin corresponding to the size of the floc, producing the second histogram, said second histogram including a low floc size bin containing one or more flocs representing the smallest flocs within the image and a high floc size bin containing one or more flocs representing the largest flocs within the image;
multiplying the mathematical formation index by a first value corresponding to an acceptable floc distribution of the web to produce a normalized mathematical formation index;
summing the number of floc size bins between the low floc size bin and the high floc size bin, inclusive, to produce a second value; and
dividing the normalized mathematical formation index by the second value to produce a mathematical formation index representative of the distribution of flocs within the image.

15. A method of measuring visual properties of a moving web having oppositely oriented first and second surfaces, the method comprising the steps of:
illuminating a two-dimensional section of a first surface of the web with light, at least a portion of said light penetrating said web and exiting the web at a two-dimensional section of a second surface of the web oppositely oriented to said first surface of the web, producing transmitted light distributed across the two-dimensional section, said distribution of transmitted light corresponding to a range of graylevel values having a minimum graylevel value and a maximum graylevel value;

producing analog video signals from the transmitted light corresponding to a full frame video image of the two-dimensional section of the second surface, each of said analog video signals representing the intensity of transmitted light at a position of the two-dimensional section of the second surface;

digitizing said analog video signals to produce digital video signals, each of said digital video signals representing a graylevel value corresponding to the intensity of the transmitted light;

analyzing the digital video signals to produce an optical distribution of the transmitted light throughout the two-dimensional section of the second surface and generating a first histogram representing the distribution of graylevel values within the image by;
  partitioning said range of graylevel values to produce a plurality of graylevel bins, each of said graylevel bins containing two or more consecutive graylevels; and
  allocating each of said digital video signals to a bin corresponding to the graylevel value of the digital video signal, producing said optical distribution of the transmitted light;

producing a mathematical formation index from the optical distribution, said index corresponding to a human visual ranking of the two-dimensional section of the second surface of the web, said mathematical formation index being produced by;
  identifying a mean graylevel bin of the first histogram;
  summing the number of digital video signals allocated to the mean graylevel bin, producing a first number;
  summing the number of bins that contain more than a predetermined number of digital video signals, producing a second number; and
  dividing the first number by the second number to produce said mathematical formation index;

generating a second histogram representing the size distribution of voids within the image by:
  determining a void threshold value;
  comparing the void threshold value to each of said digital video signals;
  eliminating all digital video signals having a graylevel value less than the void threshold so that only void video signals remain;
  designating groups of contiguous ones of the void video signals as voids;
  determining a void size threshold;
  determining a void surface area within a range of surface areas for each designated void;
  comparing the void size threshold to the surface area of each void;
  eliminating all voids having a surface area less than said size threshold;
  partitioning said range of surface areas to produce a plurality of void size bins, each of said void size bins containing a subrange within the range of void sizes; and
  allocating each of said voids to a void size bin corresponding to the size of the void, producing the second histogram, said second histogram including a low void size bin containing one or more voids representing the smallest voids within the image and a high void size bin containing one or more voids representing the largest voids within the image;

multiplying the mathematical formation index by a first value corresponding to an acceptable void distribution of the web to produce a normalized mathematical formation index;

summing the number of void size bins between the low void size bin and the high void size bin, inclusive, to produce a second value; and dividing the normalized mathematical formation index by the second value to produce a mathematical formation index representative of the distribution of voids within the image.

16. A method of measuring visual properties of a moving web having oppositely oriented first and second surfaces, the method comprising the steps of:

illuminating a two-dimensional section of a first surface of the web with only near IR wavelength light, at least a portion of said light penetrating said web and exiting the web at a two-dimensional section of a second surface of the web oppositely oriented to said first surface of the web, producing transmitted light distributed across the two-dimensional section, said distribution of transmitted light corresponding to a range of graylevel values having a minimum graylevel value and a maximum graylevel value;

producing analog video signals from the transmitted light corresponding to a full frame video image of the two-dimensional section of the second surface, each of said analog video signals representing the intensity of transmitted light at a position of the two-dimensional section of the second surface;

digitizing said analog video signals to produce digital video signals, each of said digital video signals representing a graylevel value corresponding to the intensity of the transmitted light;

analyzing the digital video signals to produce an optical distribution of the transmitted light throughout the two-dimensional section of the second surface; and producing a mathematical formation index from the optical distribution, said index corresponding to a human visual ranking of the two-dimensional section of the second surface of the web.

17. A method of on-line control of paper production process variables to obtain desired visual properties of a moving, uncoated web of paper having oppositely oriented first and second surfaces, the method comprising the steps of:

illuminating a two-dimensional section of a first surface of the moving web with light, at least a portion of said light penetrating said web and exiting the web at a two-dimensional section of a second surface of the web oppositely oriented to said first surface of the web, producing transmitted light distributed across the two-dimensional section, said distribution of transmitted light corresponding to a range of graylevel values having a minimum graylevel value and a maximum graylevel value;

producing analog video signals from the transmitted light corresponding to a full frame video image of the two-dimensional section of the second surface, each of said analog video signals representing the intensity of transmitted light at a position of the two-dimensional section of the second surface;

digitizing said analog video signals to produce digital video signals, each of said digital video signals representing a graylevel value corresponding to the intensity of the transmitted light;

analyzing the digital video signals to produce an optical distribution of the transmitted light throughout the two-dimensional section of the second surface;

producing a mathematical formation index corresponding to formation consistency in the web from the optical distribution, said index corresponding to a human visual ranking of the two-dimensional section of the second surface of the web; and adjusting paper production process variables to maximize said formation index.

* * * * *